United States Patent
Choi et al.

(10) Patent No.: US 12,102,442 B2
(45) Date of Patent: Oct. 1, 2024

(54) DEVICE FOR MEASURING AMOUNT OF PERSPIRATION WITH REGARD TO EACH PART OF HUMAN BODY BY USING CHANGE IN BRIGHTNESS AND METHOD FOR MEASURING AMOUNT OF PERSPIRATION

(71) Applicant: Yong Hak Choi, Seoul (KR)

(72) Inventors: Yong Hak Choi, Seoul (KR); Se Joong Oh, Suwon-si (KR); Eun Kyung Lee, Seongnam-si (KR); Gang Ho Goh, Seongnam-si (KR); Seung Hee Choi, Seongnam-si (KR); Ro Bin Yim, Seoul (KR)

(73) Assignee: Yong Hak Choi, Seoul (KR)

( * ) Notice: Subject to any disclaimer, the term of this patent is extended or adjusted under 35 U.S.C. 154(b) by 652 days.

(21) Appl. No.: 17/424,898

(22) PCT Filed: Aug. 9, 2019

(86) PCT No.: PCT/KR2019/010118
§ 371 (c)(1),
(2) Date: Jul. 22, 2021

(87) PCT Pub. No.: WO2020/209449
PCT Pub. Date: Oct. 15, 2020

(65) Prior Publication Data
US 2022/0079508 A1    Mar. 17, 2022

(30) Foreign Application Priority Data
Apr. 8, 2019 (KR) .................. 10-2019-0040998

(51) Int. Cl.
*A61B 5/00* (2006.01)
*A61B 5/01* (2006.01)
(Continued)

(52) U.S. Cl.
CPC .......... *A61B 5/4266* (2013.01); *A61B 5/0075* (2013.01); *A61B 5/1032* (2013.01);
(Continued)

(58) Field of Classification Search
CPC ... A61B 5/4266; A61B 5/0075; A61B 5/1032; A61B 5/00; A61B 5/01; A61B 5/0059;
(Continued)

(56) References Cited

U.S. PATENT DOCUMENTS 9,228,986 B2 * 1/2016 Xiao ...................... G01N 31/22
2012/0309047 A1 * 12/2012 Kofinas .................. G01N 21/78
436/95

(Continued)

FOREIGN PATENT DOCUMENTS

JP    2006-296816 A    11/2006
JP    2009-213728 A    9/2009
(Continued)

OTHER PUBLICATIONS

Google machine translation of JP2009213728A (Year: 2009).*
(Continued)

*Primary Examiner* — Alex M Valvis
*Assistant Examiner* — Justin Xu

(57) ABSTRACT

Provided is a device for measuring an amount of perspiration of respective body parts of a person using a change in brightness, including: a temperature controller which raises temperature of a subject and induces sweating; a covering which is coated with a perspiration reagent and is in contact with a skin of the subject, wherein the perspiration reagent absorbs perspiration and changes its color in response to perspiration; a light irradiator which irradiates light to the covering; a reflected light collector which collects reflected light reflected from the covering; a brightness change measurer which measures a change in brightness of the reflected
(Continued)

light collected by the reflected light collector; and a perspiration amount converter which converts the change in brightness to an amount of perspiration secreted from respective body parts of the subject.

6 Claims, 4 Drawing Sheets

(51) Int. Cl.
| | |
|---|---|
| A61B 5/103 | (2006.01) |
| G01J 5/48 | (2022.01) |
| G01N 21/55 | (2014.01) |
| G01N 21/78 | (2006.01) |
| H04N 23/56 | (2023.01) |

(52) U.S. Cl.
CPC ............. *G01N 21/55* (2013.01); *G01N 21/78* (2013.01); *H04N 23/56* (2023.01)

(58) Field of Classification Search
CPC ........ G01N 21/55; G01N 21/78; H04N 23/56; H04N 5/33; G01J 5/48
See application file for complete search history.

(56) References Cited

U.S. PATENT DOCUMENTS

| | | | |
|---|---|---|---|
| 2017/0079599 A1* | 3/2017 | Yoshida | ................. G06T 7/0012 |
| 2018/0136191 A1* | 5/2018 | Asvadi | ................. A61B 5/4266 |
| 2018/0284092 A1* | 10/2018 | Tong | ....................... B65D 81/34 |
| 2020/0129112 A1* | 4/2020 | Model | .................... G16H 20/00 |
| 2020/0155047 A1* | 5/2020 | Rogers | ................. A61B 5/1477 |
| 2022/0015688 A1* | 1/2022 | Larson | ................. A61B 5/1468 |

FOREIGN PATENT DOCUMENTS

| | | |
|---|---|---|
| JP | 2010046196 A | 3/2010 |
| KR | 10-0588306 B1 | 6/2006 |
| KR | 10-2015-0117071 A | 10/2015 |
| KR | 10-2015-0141197 A | 12/2015 |
| KR | 10-2016-0108054 A | 9/2016 |

OTHER PUBLICATIONS

International Search Report of PCT/KR2019/010118 published on Oct. 15, 2020.
Written opinion of PCT/KR2019/010118 published on Oct. 15, 2020.

\* cited by examiner

DEVICE FOR MEASURING AMOUNT OF PERSPIRATION WITH REGARD TO EACH PART OF HUMAN BODY BY USING CHANGE IN BRIGHTNESS AND METHOD FOR MEASURING AMOUNT OF PERSPIRATION

TECHNICAL FIELD

The present invention relates to a device and a method for measuring the amount of perspiration of a human body using a change in brightness.

More particularly, it relates to a device and a method of irradiating light on a covering; collecting a first reflected light from the covering; precisely detecting a change in brightness at respective body parts of a subject before and after sweating; and converts the change in brightness to an amount of perspiration. The covering is coated with a perspiration reagent and is in contact with skin of the subject. The perspiration reagent absorbs perspiration and changes its color in response to the perspiration absorbed.

BACKGROUND OF INVENTION

Dysfunction of the autonomic nervous system can be seen in various diseases. In certain diseases, symptoms may appear due to selective invasion of the autonomic nervous system. Because the anatomical and biological structure of the autonomic nervous system is very complex and diverse, symptoms caused by dysfunction of the autonomic nervous system can be also very complex and diverse, making diagnosis of dysfunction of the autonomic nervous system one of very difficult tasks.

The autonomic nervous system can be categorized into the sympathetic nervous system and the parasympathetic nervous system, and further sub-categorized by the specific characteristics of the nervous system. Whether an abnormality has occurred in the subdivided nervous system can be determined by examining each individual nervous system, thereby locating the damaged location. Once the damaged location and the degree of damage are found, a proper treatment method can be determined.

However, such a detailed examination of the nervous system is time-consuming and costly, and such examination method is complicated.

Considering these problems, studies on the examination of perspiration reaction through body temperature control are actively being conducted to develop an efficient method of examining the autonomic nervous system.

The examination of the perspiration reaction through body temperature control detects local sweating and determines abnormality of the autonomic nervous system through the localized sweating.

In conventional tests for perspiration reaction through body temperature control, a color development reagent is directly applied to the skin of a subject to induce a perspiration reaction. Then, a change in the color development reagent by the secreted sweat was examined.

In the conventional method, the color development reagent must be directly applied to the skin. The subject feels bad and has a great resistance to applying the color development reagent to the entire skin. In addition, the subject feels uncomfortable since the subject's skin becomes dirty after the test due to the color development reagent directly applied onto the skin.

In particular, during the perspiration reaction test, the perspiration secreted from a given location of the body may move to another location of the body where sweating does not actually occur. This causes the color development reagent applied in the other location to also change, causing an error in the test.

In addition, once the perspiration reaction occurs in a given location of the body and the color of the reagent changes in the given location, additional change during the perspiration state cannot be figured out in the given location any more. Thus, it is impossible to quantitatively determine the amount of perspiration in the given location.

In other words, the conventional examination system of the perspiration reaction by body temperature control can merely determine the presence or absence of perspiration. It does not provide information on a specific amount of perspiration secreted. This makes it difficult to determine the condition of a given body part of the subject since a quantitative amount of perspiration from the given body part is not detectable.

Korean Patent Publication No. 10-2016-0108054 discloses a conventional art related to a device for detecting perspiration.

According to the conventional art, a perspiration detecting device detects sweat on a subject's skin. It includes a perspiration inducing unit that applies heat to the subject's skin; a perspiration detecting sensor unit that detects sweat secreted from the subject's skin; a sweat data generation unit that generates sweat gland data acquired from the perspiration detection sensor unit; a sweat storage unit that stores the sweat gland data on a number of pre-registered subjects; a sweat inquiry unit for inquiring whether or not a given sweat gland data is registered in the sweat storage unit; and an authentication unit for authenticating the subject according to a search result of the sweat inquiry unit.

The conventional art merely detects the presence or absence of perspiration and uses this information. That is, the system presented in the conventional art merely determines the presence or absence of perspiration, and cannot detect a specific amount of perspiration at issue.

In addition, the conventional system cannot determine the amount of perspiration from respective body parts. Thus, it is difficult to determine the individual states of respective body parts in detail.

DETAILED DESCRIPTION OF THE INVENTION

Problems to be Solved

The present invention is proposed to solve the conventional problems as described above. An objective of the present invention is to provide a device and a method for measuring the amount of perspiration from respective parts of a subject using a change in brightness. The present invention uses a covering which is coated with a perspiration reagent and is in contact with the skin of a subject. The perspiration reagent absorbs perspiration secreted and changes its color in response to the perspiration absorbed. By applying the color development reagent onto the covering, rather than directly onto the skin of the subject, this invention (i) can reduce resistance of the subject and (ii) can keep the skin of the subject clean even after the test. According to the present invention, substantially no color development reagent remains on the skin of the subject after the test.

The present invention provides a device and a method for measuring the amount of perspiration of a human body using a change in brightness. Quantitative detection of the amount of perspiration can be conducted in addition to determining the presence of perspiration. The state of a given body part can be determined based on the amount of perspiration of the given body part.

The present invention, which provides a device and a method for measuring the amount of perspiration of a human body using a change in brightness, uses a covering in a light blue color. A perspiration reagent includes an aqueous ink. The aqueous ink contains acrylic resin. The aqueous ink is applied to the covering. Reduction in the brightness index on the covering is observed at multiple perspiration reference points. Depending on perspiration states, the multiple perspiration reference points are categorized to insufficient perspiration state, normal perspiration state, and sufficient perspiration state. With this system, it is possible to determine relative health states of a number of body parts of a subject at once.

SUMMARY OF INVENTION

To solve the problems, a device for measuring an amount of perspiration of respective body parts of a person using a change in brightness is provided. The device includes: a temperature controller which raises temperature of a body part of a subject and induces sweating; a covering which is coated with a perspiration reagent and is in contact with a skin of the subject, wherein the perspiration reagent absorbs perspiration and changes its color in response to perspiration; a light irradiator which irradiates light to the covering; a reflected light collector which collects reflected light reflected from the covering; a brightness change measurer which measures a change in brightness of the reflected light collected by the reflected light collector; and a perspiration amount converter which converts the change in brightness to an amount of perspiration of the body part of the subject.

To this end, a method for measuring an amount of perspiration of respective body parts of a subject using a change in brightness is provided. The method includes: a step of placing a covering on a body part of a subject to be in contact with each other, wherein the covering is coated with a perspiration reagent, wherein the perspiration reagent absorbs perspiration and changes its color in response to perspiration; a step of irradiating light to the covering before sweating; a step of collecting a first reflected light, wherein the first reflected light is reflected from the covering before sweating; a step of measuring a first brightness of the first reflected light; a step of raising body temperature of the subject and induces sweating; a step of irradiating light to the covering after sweating, wherein the covering is subject to change its color upon absorption of perspiration; a step of collecting a second reflected light which is reflected from the covering after sweating; a step of measuring a second brightness of the second reflected light; and a step of detecting a change between the first brightness and the second brightness, and converting the change in brightness to an amount of perspiration of the body part of the subject.

Advantages of Invention

As described above, the device and the method according to the present invention, which measure the amount of perspiration of a human body by using a change in brightness, have the following advantages.

First, the present invention can prevent a color development reagent from being applied directly onto the entire skin of a subject, thereby reducing subject's resistance. The perspiration reagent is coated on a covering, and the covering is in contact with a skin of the subject. The perspiration reagent absorbs sweat secreted and changes its color and consequently changes the color of the covering in response to the sweat.

An after-test procedure such as a shower is unnecessary since no color development reagent remains on the skin of the subject after the test. That is, the skin of the subject can be maintained clean even after the test.

Second, the present invention can specifically determine simultaneously the states of multiple body parts and the degree of abnormality of the autonomic nervous system based on quantitative detection of the amount of perspiration at the multiple body parts, in addition to the determination of the presence of perspiration, even without a complex and detailed examination of the nervous system that is time-consuming and costly.

Third, according to the present invention, a covering in light blue color, to which a perspiration reagent having aqueous ink containing acrylic resin is applied, is used. A normal state is subcategorized into a first perspiration reference point, a second perspiration reference point, and a third perspiration reference point. With this, the present invention can collectively determine relative health states of multiple body parts of a subject.

BEST MODE

In the present invention, the accompanying drawings may be exaggerated for better clarity, better comparison with the conventional art, and for better understanding of the technology at issue. Terms are defined in consideration of functions in the present invention. Terms may be construed differently depending on intentions or customs of a user who handles and operates the system. Thus, definition of the terms should be determined based on the technical idea throughout the specification of the present invention.

The embodiments are merely examples of devices and methods presented in the claims of the present invention and should not be construed to limit the scope of the present invention. The scope of this invention should be construed in view of the technical idea presented throughout the specification of the present invention. In describing the present invention, a detailed description of a known configuration or function may be omitted for better understanding of the present invention.

Figure 1:
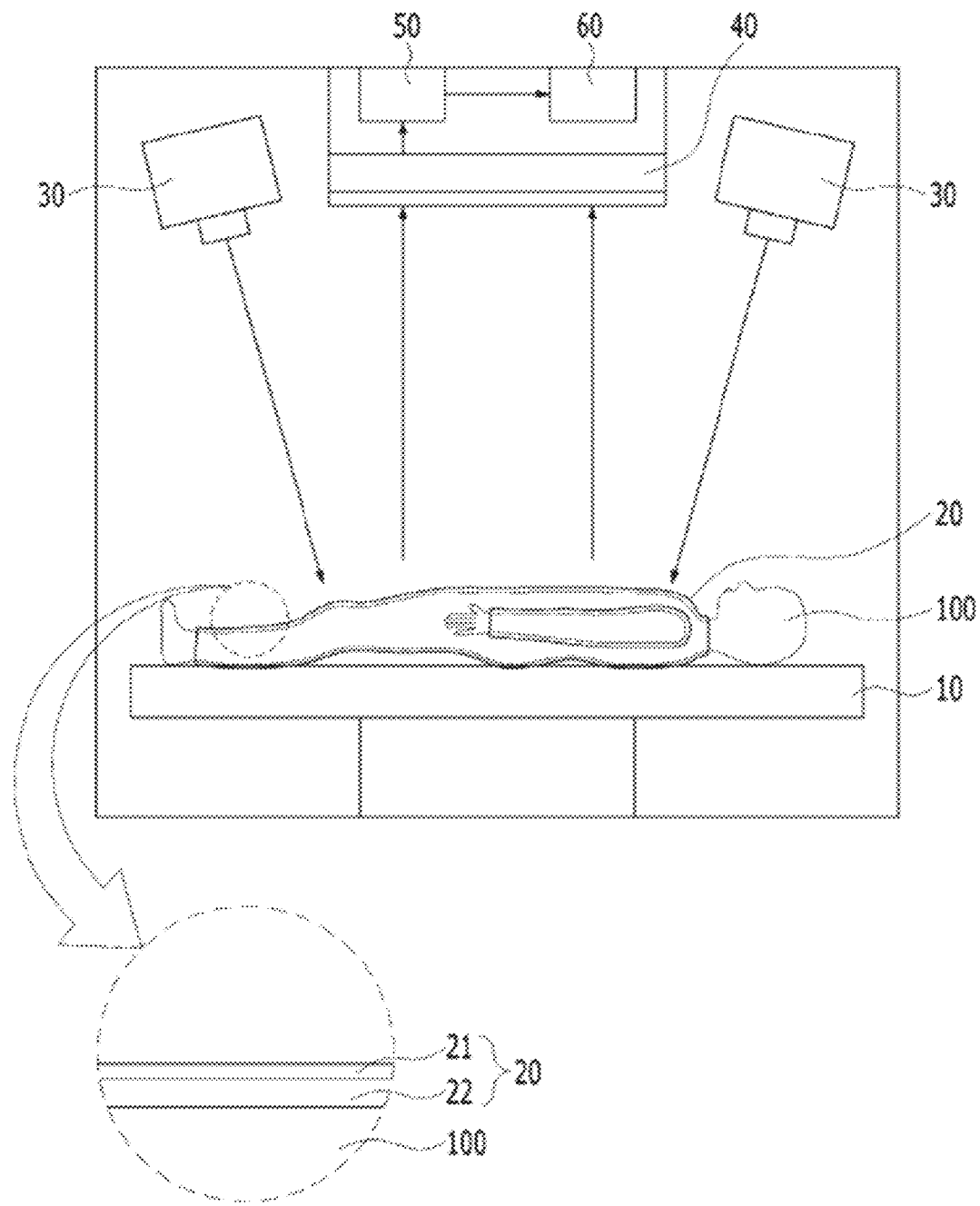
FIG. 1 is a block diagram showing a device according to the present invention for measuring the amount of perspiration of respective body parts of a person using a change in brightness.

FIG. 1 is a block diagram showing a device according to the present invention for measuring the amount of perspiration of a human body using a change in brightness. According to FIG. 1, the device for measuring the amount of perspiration of a human body using a change in brightness includes: a temperature controller (10) for raising body temperature of a subject (100) and induces sweating; a covering (20) coated with a perspiration reagent and in contact with a skin of the subject, wherein the perspiration reagent absorbs perspiration and changes its color in response to the perspiration secreted; a light irradiator (30) for irradiating light to the covering; a reflected light collector (40) for collecting reflected light which is reflected from the covering; a brightness change measurer (50) for measuring a change in brightness of the reflected light collected by the reflected light collector; and a perspiration amount converter (60) for converting the change in brightness into an amount of perspiration secreted from the subject.

The temperature controller (10) can be any device so long as it can induce perspiration by increasing the body temperature of the subject (100). Two types of temperature control can be considered. The first type is to induce perspiration by increasing the body temperature through a direct contact with the subject (100). The second type is to induce perspiration by increasing the body temperature by increasing the temperature of the space where the subject (100) is located to increase the body temperature of the subject (100) without a direct contact with the subject (100).

Any type of temperature control can serve the temperature controller (10) so long as it can increase the body temperature of the subject (100). For example, a hot wire method, a hot water method, a hot air method, or an infrared method can work to this end. The body temperature of the subject (100) refers to the central body temperature, which is the temperature of blood flowing from the heart. It is preferable, in the present invention, to induce perspiration by raising the central body temperature. It is preferable to use an infrared ray to increase the central body temperature.

The covering (20) is in contact with the skin of the subject (100), blocks external light, and is coated with a perspiration reagent. The perspiration reagent absorbs perspiration and changes its color in response to the perspiration absorbed. In general, it is desirable that the covering is made of a fabric which can absorb perspiration. The fabric may include a natural fabric or an artificial fabric. It is preferable that the fabric has elasticity so as to be in close contact with the skin of the subject (100). The covering (20) with elasticity can be in close contact with the skin, and thus the exact location at which perspiration is absorbed is detectable.

The covering (20) may be prepared by applying a perspiration reagent on a fabric. The perspiration reagent absorbs perspiration and changes its color in response to the amount of the perspiration absorbed. Any reagent can serve as the perspiration reagent so long as it can change its color in response to absorption of perspiration.

In general, when applied onto a fabric, the initial color of the perspiration reagent is white. The color of the perspiration reagent changes into transparent when perspiration is absorbed. Once sweat or perspiration is absorbed, the color of the covering (20) made of the fabric changes its color from a light color into a dark color. In this way, a change in brightness occurs apparently when sweat or perspiration is absorbed. That is, the perspiration reagent which is applied on the fabric changes its color from white to transparent, and the covering (20) made of the fabric changes its color from a light color to a dark color, In the present invention, (i) the brightness of the covering (20) coated with the perspiration reagent is detected before sweating and after sweating, (ii) the difference in brightness between before-sweating and after-sweating, and (iii) the difference in brightness is converted into the amount of perspiration secreted. In this way, relative health states of multiple body parts of the subject (100) can be determined using the amount of perspiration. Any device can serve as the light irradiator (30) so long as it can irradiate light to the covering (20) worn by the subject (100). In the present invention, it is preferable that the light irradiator (30) irradiates visible light to the covering (20) worn by the subject (100). To this end, it is preferable that the light irradiator (30) is a visible light irradiator that generates visible light.

The reflected light collector (40) collects light reflected from the covering (20) worn by the subject (100) upon irradiation. As described above, in the present invention, the light irradiator (30) preferably irradiates visible light to the covering (20) worn by the subject (100). So it is preferable that the reflected light collector (40) is also a device that collects visible light. To this end, it is preferable that the reflected light collector (40) is a reflected visible light collector which collects visible light reflected. The reflected visible light collector may be an optical sensor or a camera.

The brightness change measurer (50) measures a change in brightness. The change in brightness occurs (i) when the perspiration reagent applied on the fabric changes its color from white to transparent upon absorption of perspiration and thereby (ii) when the covering (20) made of fabric changes its color from light color to dark color upon absorption of perspiration.

Before sweating, the light irradiator (30) irradiates light to the covering (20) coated the perspiration reagent. The reflected light collector (40) collects a first reflected light which is reflected from the covering before sweating. The brightness change measurer (50) measures a first brightness of the first reflected light. Likewise, after sweating, the light irradiator (30) irradiates light to the covering (20) coated with the perspiration reagent. The reflected light collector (40) collects a second reflected light which is reflected from the covering after sweating. The brightness change measurer (50) measures a second brightness of the second reflected light. In this way, the brightness change measurer (50) measures the first brightness of the first reflected light and the second brightness of the second reflected light and automatically detects a change between the first brightness and the second brightness.

Using the information on the change in brightness which is measured by the brightness change measurer (50), the perspiration amount converter (60) automatically calculates and converts the information to the amount of perspiration of a given body part. When the change in brightness (or a change in brightness reduction) is small at the given body part of the subject (100), it can be interpreted that a small amount of perspiration occurred at the given body part. The amount of perspiration can be converted to a relatively small value.

In contrast, when the change in brightness (or the change in brightness reduction) is large at the given part of the subject (100), it can be interpreted that a large amount of perspiration occurred in the given body part. The amount of perspiration can be converted to a relatively large value. If the change in brightness reduction at the given body part of the subject (100) is zero ("0"), it can be interpreted that perspiration has not occurred at the given body part, and the amount of perspiration can be converted to zero ("0"). The reference data for converting a change in the brightness to the amount of perspiration secreted may be stored in the perspiration amount converter (60) in advance.

Since the reference data for converting a change in the brightness to the amount of perspiration secreted may change depending on the type of the perspiration reagent, the thickness of the perspiration reagent coating layer, and the thickness and the type of the fabric layer of the covering (20) worn by the subject (100). Considering such changes, it is desirable to prepare various reference data for a change in the brightness to the amount of perspiration secreted.

The reference data a change in the brightness to the amount of perspiration secreted may change according to the surrounding environment (temperature, humidity, etc.), as well. Thus, calibration data according to the surrounding environment (temperature, humidity, etc.) can be also stored in the perspiration amount converter (60) in advance. Using the pre-stored reference data and calibration data, the amount of perspiration can be immediately calculated from the information on the change in brightness.

The covering (20) refers to an object that blocks external light by contacting the skin of the subject (100) and is coated with a perspiration reagent. The perspiration reagent includes aqueous ink containing acrylic resin, absorbs sweat secreted, and changes its color. Acrylic resin refers to a synthetic resin obtained by polymerization of acrylic acid and its derivatives. The aqueous ink containing acrylic resin is preferably white in color when applied to the fabric. The white perspiration reagent is preferably applied onto a blue fabric. When the white perspiration reagent is applied on the blue fabric, the covering (20) has a light blue color. Light blue refers to a color with color symbols 2.5B~10B according to the Munsell color coding method.

(i) The perspiration reagent including the aqueous ink changes its color to be transparent when it absorbs sweat secreted. When sweat is absorbed, the covering (20) made of fabric changes its color from a light color to a dark color. The change in color of the perspiration reagent from white to transparent and (ii) the change in color of the covering (20) from light color to dark color, in combination, result in brightness reduction at the given body part of the subject (100).

In the present invention, it is preferable that the covering (20) has a light blue color when coated by the perspiration reagent having aqueous ink. It is because a change in brightness between before-sweating and after-sweating is seen clearly at the perspiration reference points when the covering (20) has the light blue color.

Repeatedly, the covering (20) is preferred to have a light blue color when coated with the perspiration reagent in that the change in brightness can be observed clearly at the first, the second, and the third perspiration reference points. The change in brightness is measured by the brightness change measurer (50). The first, the second, and the third perspiration reference points may be pre-set.

In the present invention, the first, the second, and the third perspiration reference points are classified in reference to the amount of perspiration. The first perspiration reference point is defined as the point where the amount of perspiration secreted from a given body part is 1.95 μl/cm$^2$. The second perspiration reference point is defined as the point where the amount of perspiration secreted from a given body part is 2.45 l/cm$^2$. The third perspiration reference point is defined as the point where the amount of perspiration secreted from a given body part is 3.00 μl/cm$^2$ in the body part. In addition, it is preferable that the covering (20) includes a perspiration reagent coating layer (21) of 0.03-0.08 mm in thickness and a fabric layer (22) of 0.20-0.40 mm in thickness.

When the perspiration reagent coating layer (21) is less than 0.03 mm in thickness, the degree of color change due to absorption of perspiration is insufficient. Thus, the amount of perspiration measured using the change in brightness may be inaccurate. When the perspiration reagent coating layer (21) exceeds 0.08 mm in thickness, the air permeability of the fabric layer is too low. The covering (20) may block the perspiration glands of the subject (100). This may distort the perspiration pattern and make inaccurate the amount of perspiration measured based on the change in brightness.

When the fabric layer (22) is less than 0.20 mm in thickness, the absorption of sweat is insufficient and the degree of change in color may not be seen clearly. This may make inaccurate the measurement of the amount of perspiration using the change in brightness. When the fabric layer (22) exceeds 0.40 mm in thickness, the air permeability of the fabric layer (20) becomes too low, causing the covering (20) to block the perspiration glands of the subject (100). When the fabric layer (22) is too thick, the sweat secreted may not be sufficiently transmitted to the perspiration reagent coating layer. This may distort the perspiration pattern and may prevent accurate measurement of the amount of perspiration measured based on the change in brightness.

In the present invention, the fact that the amount of perspiration is at the first perspiration reference point, i.e., 1.95 μl/cm$^2$ or more indicates the body part under examination is at a normal perspiration state. However, the fact that the amount of perspiration is between the first perspiration reference point, i.e., 1.95 μl/cm$^2$ and the second perspiration reference point, i.e., 2.45 μl/cm$^2$ indicates the body is currently in a normal state but there is some risk that the amount of perspiration drops below the first perspiration reference point. Thus, abnormalities may occur in the body part in the future.

In the present invention, the second perspiration reference point refers to the point when the amount of perspiration is 2.45 μl/cm$^2$. The fact that the amount of perspiration is at the second perspiration reference point, i.e., 2.45 μl/cm$^2$ or more indicates the body is currently in a normal state and also there is substantially no risk that the amount of perspiration drops below the first perspiration reference point. Thus, there is substantially no risk that abnormalities may occur at the body part in the future. The fact that the amount of perspiration is more than the second perspiration reference point, i.e., 2.45 μl/cm$^2$, but less than the third perspiration reference point, i.e., 3.00 μl/cm$^2$ indicates the body part is in an unbalanced state compared to other body parts of the amount of perspiration is above the third perspiration reference point.

In addition, the fact that the amount of perspiration is more than the second perspiration reference point, i.e., 3.00 μl/cm$^2$ or more indicates the body is in a normal state and in a sufficient and balanced perspiration state. It also indicates that the body there is substantially no risk that abnormalities may occur at the body part in the future. This further indicates that perspiration balance of the whole body is sufficiently established. In a normal body condition, the amounts of perspiration from the left and right sides of the body are almost the same as each other.

Assume that (i) the first perspiration reference point is 1.95 μl/cm$^2$ or more in both of the left and right sides of a given body part. When (i) the left side of the given body part is between the first perspiration reference point, i.e., 1.95 μl/cm$^2$, and the second perspiration reference point, i.e., 2.45 μl/cm$^2$, and (ii) the right side of the given body part is between the second perspiration reference point, i.e., 2.45 μl/cm$^2$, and the third perspiration reference point, i.e., 3.00 μl/cm$^2$, it can be said that the left and right sides of the given body part are in an unbalanced state. Thus, overall balance care for the body is necessary.

The left side of the given body part is currently in normal perspiration state. However, it can be said that its perspiration state might fall below the first perspiration reference point in the future. That is, there is some risk that abnormalities may occur in the left side of the given body part. Thus, the left side of the given body part needs care. Under a normal body condition, the amounts of perspiration from respective body parts are almost the same as each other.

Assume that (i) the amount of perspiration at a given part is between the second perspiration reference point, i.e., 2.45 µl/cm$^2$ (inclusive) and the third perspiration reference point, i.e., 3.00 µl/cm$^2$ (exclusive), and (ii) the amount of perspiration at all remaining body parts a given part is the third perspiration reference point, 3.00 µl/cm$^2$ or more. It can be said that the given body part is in an unbalanced state. Care and treatment for the balance of the overall body can be taken as a preventive measure.

BEST MODE

The perspiration reagent has aqueous ink. The aqueous ink contains acrylic resin. The following experiments are performed to confirm the fact that a brightness change can be more clearly observed around the first, the second and the third perspiration reference points when the covering (20) coated with the perspiration reagent has a light blue color. The brightness change is measured by brightness change measurer (50).

Coverings (20) in various colors, light blue, dark blue, dark green, light red, indigo, purple, white, and black, are prepared. The colors are identified when the coverings are coated with the perspiration reagent. The brightness changes of the respective coverings are measured.

EXPERIMENTAL EXAMPLE

A covering (20) coated with a perspiration reagent was prepared. The coverings were in color of light blue (Munsell color code: 7.5B), dark blue (Munsell color code: 2.5PB), dark green (Munsell color code: 2.5G), light red (Munsell color code: 7.5R), indigo (Munsell color code: 10BG), purple ((Munsell color code: 7.5P), white (Munsell color symbol: N), and black (Munsell color symbol: N), respectively. Changes in brightness of the coverings were measured.

The brightness of the coverings change depending on the amount of perspiration absorbed. The perspiration reagent includes an aqueous ink containing acrylic resin. The change in brightness was confirmed by measuring the brightness index L* of the color system L*a*b*. The L*a*b* color system is based on research to approach human sensibility. The L*a*b* color system is a color space defined by the International Lighting Commission based on the opposite color theory of yellow-blue, green-red perceived by humans.

L* is reflectance (brightness) which represents the same brightness as human visual perception and can also be expressed in units of decimal places 0-100. a* is a chromaticity diagram. Here, +a* represents the red color value direction and –a* represents the green color value direction. b* is another chromaticity diagram. Here, +b* represents the yellow value direction and –b* represents the blue value direction.

Tables 1 to 8 show the changes in the brightness index L* of the covering (20) in various colors. The covering (20) is coated with a perspiration reagent and colored in light blue, dark blue, dark green, light red, indigo, purple, white, and black, respectively. The perspiration reagent includes an aqueous ink containing acrylic resin. The brightness index L* changes depending on the amount of perspiration secreted.

TABLE 1

| Color | perspiration(µl/cm$^2$) | L* | a* | b* |
|---|---|---|---|---|
| Light Blue | 0.2 | 94 | −31 | −10 |
| | 0.7 | 92 | −42 | −13 |
| | 1.8 | 92 | −42 | −13 |
| | 2.0 | 76 | −27 | −37 |
| | 2.5 | 61 | −2 | −60 |
| | 2.7 | 61 | −2 | −60 |
| | 3.1 | 44 | 11 | −59 |
| | 3.3 | 44 | 11 | −59 |
| | 3.5 | 44 | 11 | −59 |
| | 3.6 | 44 | 11 | −59 |

TABLE 2

| Color | Perspiration(µl/cm$^2$) | L* | a* | b* |
|---|---|---|---|---|
| Dark Blue | 0.2 | 84 | −24 | −25 |
| | 0.4 | 77 | −20 | −35 |
| | 0.7 | 59 | −17 | −35 |
| | 1.8 | 44 | 11 | −59 |
| | 2.0 | 44 | 11 | −59 |
| | 2.5 | 42 | −5 | −33 |
| | 2.7 | 42 | −5 | −33 |
| | 2.9 | 42 | −5 | −33 |
| | 3.0 | 42 | −5 | −33 |

TABLE 3

| Color | Perspiration(µl/cm$^2$) | L* | a* | b* |
|---|---|---|---|---|
| Dark Green | 0.7 | 100 | 0 | 0 |
| | 1.8 | 100 | 0 | 0 |
| | 2.0 | 96 | −17 | −6 |
| | 2.5 | 96 | −17 | −6 |
| | 2.7 | 95 | −24 | 19 |
| | 2.9 | 93 | −39 | 15 |
| | 3.0 | 92 | −46 | 39 |
| | 3.3 | 92 | −46 | 39 |
| | 3.6 | 92 | −46 | 39 |

TABLE 4

| Color | Perspiration(µl/cm$^2$) | L* | a* | b* |
|---|---|---|---|---|
| Light Red | 1.8 | 99 | −6 | 25 |
| | 2.0 | 99 | −6 | 25 |
| | 2.5 | 86 | 14 | 13 |
| | 2.7 | 86 | 14 | 13 |
| | 2.9 | 85 | 11 | 57 |
| | 4.3 | 73 | 36 | 44 |
| | 5.2 | 55 | 39 | 47 |

TABLE 5

| Color | Perspiration(µl/cm$^2$) | L* | a* | b* |
|---|---|---|---|---|
| Indigo | 1.8 | 40 | −18 | −6 |
| | 2.0 | 40 | −18 | −6 |
| | 2.5 | 40 | −18 | −6 |
| | 2.7 | 40 | −18 | −6 |
| | 2.9 | 39 | −27 | 23 |
| | 3.0 | 21 | 0 | 0 |
| | 3.2 | 21 | 0 | 0 |

TABLE 6

| Color | Perspiration (μl/cm²) | L* | a* | b* |
|---|---|---|---|---|
| Purple | 0.8 | 69 | 26 | −19 |
| | 1.5 | 69 | 26 | −19 |
| | 1.8 | 69 | 26 | −19 |
| | 2.0 | 68 | 20 | 8 |
| | 2.2 | 68 | 20 | 8 |
| | 2.3 | 68 | 20 | 8 |
| | 2.6 | 63 | 0 | 0 |
| | 3.0 | 63 | 0 | 0 |
| | 3.1 | 63 | 0 | 0 |

TABLE 7

| Color | Perspiration (μl/cm²) | L* | a* | b* |
|---|---|---|---|---|
| White | 1.8 | 100 | 0 | 0 |
| | 2.0 | 100 | 0 | 0 |
| | 2.5 | 100 | 0 | 0 |
| | 2.7 | 100 | 0 | 0 |
| | 2.9 | 100 | 0 | 0 |
| | 3.0 | 100 | 0 | 0 |
| | 3.5 | 100 | 0 | 0 |

TABLE 8

| Color | Perspiration (μl/cm²) | L* | a* | b* |
|---|---|---|---|---|
| Black | 0.2 | 60 | −18 | −6 |
| | 0.6 | 60 | −18 | −6 |
| | 1.8 | 60 | −18 | −6 |
| | 2.0 | 60 | −18 | −6 |
| | 2.2 | 60 | −18 | −6 |
| | 2.3 | 60 | −18 | −6 |
| | 2.4 | 59 | −26 | 21 |
| | 2.7 | 40 | −18 | −6 |
| | 2.9 | 39 | −27 | 23 |
| | 3.0 | 21 | 0 | 0 |
| | 3.3 | 92 | 46 | 39 |

According to tables 1 to 8, light blue, dark green, and purple colors showed apparent reduction of the brightness index at the first perspiration reference point. The perspiration amount at the first perspiration reference point is 1.95 μl/cm². Light blue, dark blue, light red, purple, and black colors showed apparent reduction of the brightness index at the second perspiration reference point. The perspiration amount at the second perspiration reference point is 2.45 μl/cm². Light blue, dark green, light red, indigo, and black colors showed apparent reduction of the brightness index at the third perspiration reference point. The perspiration amount at the third perspiration reference point is 3.00 μl/cm². Light blue is the only color which showed apparent reduction of the brightness index at all of the first, the second, and the third perspiration reference points.

As a result, only the covering (20), which has a light blue color when coated with a perspiration reagent, showed clear reduction in the brightness index at all of the first sweating reference point, the second sweating reference point, and the third sweating reference point. This makes it possible to accurately measure the amount of perspiration using the change in brightness.

Specifically, the brightness index of the covering (20), which has a light blue color when coated with a perspiration reagent, was measured by the brightness change measurer. When the brightness index of the covering (20) drops from 92 to 76, the body part showed 1.95 μl/cm² of perspiration amount which corresponds to the first sweating reference point.

The brightness index of the covering (20), which has a light blue color when coated with a perspiration reagent, was measured by the brightness change measurer. When the brightness index of the covering (20) drops from 76 to 61, the body part showed 2.45 μl/cm² of perspiration amount which corresponds to the second sweating reference point.

The brightness index of the covering (20), which has a light blue color when coated with a perspiration reagent, was measured by the brightness change measurer. When the brightness index of the covering (20) drops from 61 to 44, the body part showed 3.00 μl/cm² of perspiration amount which corresponds to the third sweating reference point.

Figure 2:
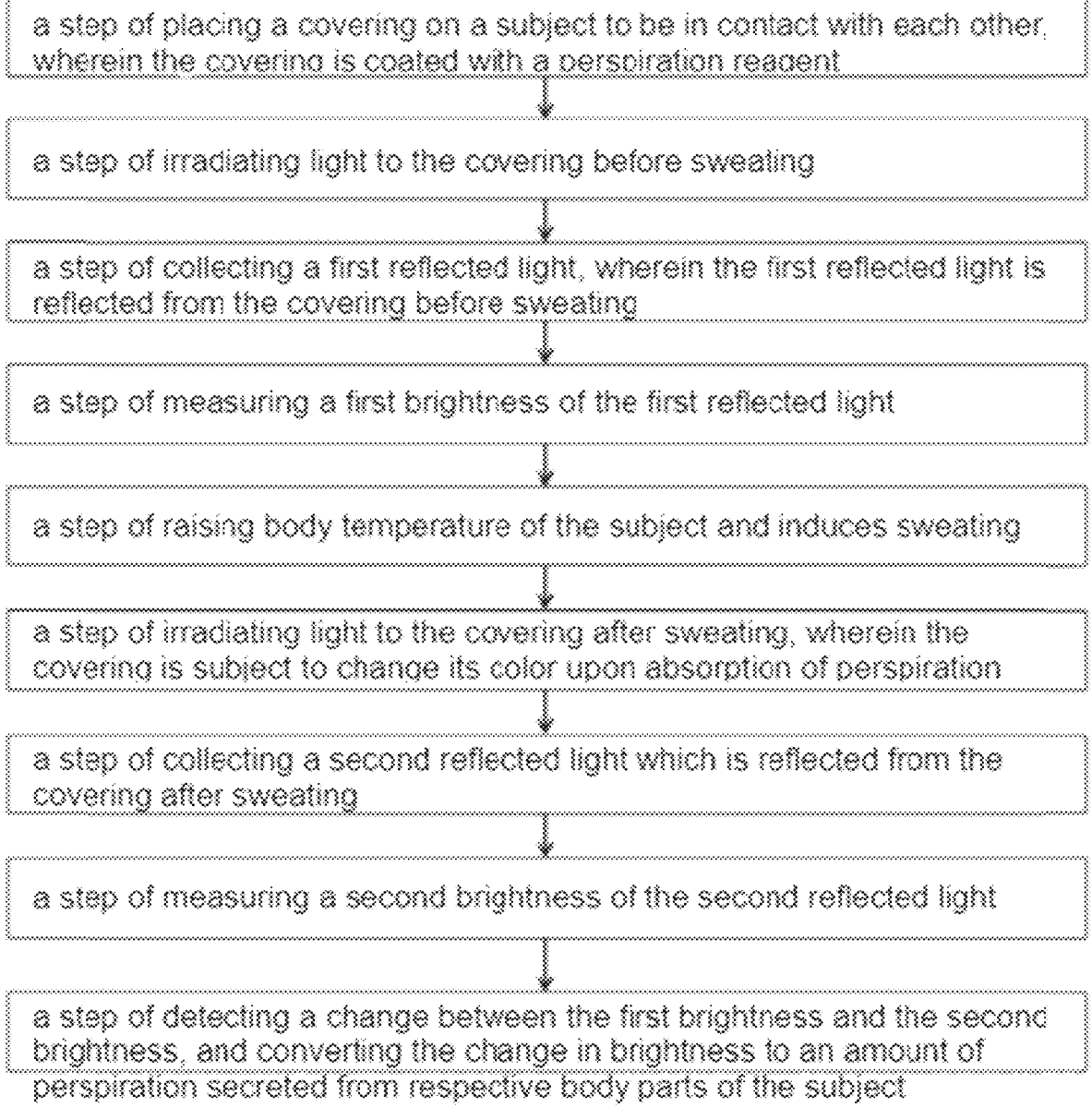
FIG. 2 is a flow chart showing a method according to the present invention for measuring the amount of perspiration of respective body parts of a person by using the brightness change.

FIG. 2 is a flow chart showing a process according to the present invention which measures the amount of perspiration at multiple parts of a human body by using a change in brightness. Referring to FIG. 2, the process includes: a step of placing a covering on a subject to be in contact with each other, wherein the covering is coated with a perspiration reagent, wherein the perspiration reagent absorbs perspiration and changes its color in response to perspiration; a step of irradiating light to the covering before sweating; a step of collecting a first reflected light, wherein the first reflected light is reflected from the covering before sweating; a step of measuring a first brightness of the first reflected light; a step of raising body temperature of the subject and induces sweating; a step of irradiating light to the covering after sweating, wherein the covering is subject to change its color upon absorption of perspiration; a step of collecting a second reflected light which is reflected from the covering after sweating; a step of measuring a second brightness of the second reflected light; and a step of detecting a change between the first brightness and the second brightness, and converting the change in brightness to an amount of perspiration secreted from respective body parts of the subject.

In the step of placing the covering (20) on the subject, the covering (20) contacts the skin of the subject (100), blocks external light, and is coated with a perspiration reagent. The perspiration reagent includes an aqueous ink containing acrylic resin and changes its color upon absorption of perspiration secreted from the subject. The covering (20) is in a light blue color when coated with the perspiration reagent.

In the step of Irradiating light to the covering before sweating, it is preferable that the light irradiator (30) irradiates visible light to the covering (20) worn by the subject (100). To this end, it is preferable that the light irradiator (30) is a visible light irradiator that generates visible light.

In the step of collecting the first reflected light, preferably, the reflected light collector (40) collects visible light. To this end, preferably, the reflected light collector (40) is a reflected visible light collector which can collect visible light.

In the step of measuring the first brightness of the first reflected light, the brightness change measurer (50) measures the brightness of the first reflected light. The first reflected light is reflected from the covering before sweating.

Repeatedly, the light irradiator (30) irradiates light to the covering (20) coated with the perspiration reagent, the reflected light collector (40) collects the first reflected light which is reflected from the covering before sweating. Then, the brightness change measurer (50) measures the brightness of the first reflected light.

In the step of raising body temperature of the subject and induces sweating, the temperature controller (10) may be employed to induce perspiration by increasing the body temperature of the subject (100). Various methods can be used such as a hot wire method, a hot water method, a hot air method, or an infrared method. Upon absorption of perspiration, a change in brightness occurs clearly. That is, the perspiration reagent, which is applied on the covering, changes its color from white to transparent. As a result, the covering changes its color from a light color to a dark color.

In the step of irradiating light to the covering after sweating, the light irradiator (30) irradiates light to the covering (20) which is discolored and has a changed brightness upon absorption of perspiration.

In the step of collecting the second reflected light which is reflected from the covering after sweating, the reflected light collector (40) collects the second reflected light reflected from the covering (20) which is discolored and has a changed brightness upon absorption of perspiration.

In the step of measuring the second brightness of the second reflected light, the brightness change measurer (50) measures the brightness of the second brightness of the second reflected light. The second reflected light is reflected from the covering (20) after sweating.

Repeatedly, the light irradiator (30) irradiates light to the covering (20) coated with the perspiration reagent, the reflected light collector (40) collects the second reflected light which is reflected from the covering (20) after sweating. Then, the brightness change measurer (50) measures the brightness of the second reflected light.

In the step of detecting a change between the first brightness and the second brightness, and converting the change in brightness to an amount of perspiration secreted from respective body parts of the subject, The brightness change measurer (50) measures the first brightness of the first reflected light of the covering (20) worn by the subject (100) and the second brightness of the second reflected light of the covering (20) worn by the subject (100). Then, the brightness change measurer (50) determines the difference in brightness and provides the difference in brightness to the perspiration amount converter (60). The perspiration amount converter (60) automatically calculates and converts the change in brightness into the amount of perspiration secreted from respective body parts of the subject.

The perspiration amount converter (60) receives in advance reference data for converting a change in brightness into an amount of perspiration. The reference data may change depending on a perspiration reagent applied onto the covering (20) worn by the subject (100), the thickness of the perspiration reagent coating layer, the thickness and the type of the fabric layer, etc. Thus, it is desirable to prepare various reference data for converting a change in brightness into an amount of perspiration.

In addition, reference data for converting a change in brightness into an amount of perspiration may also change depending on surrounding environment such as temperature, humidity, etc. Thus, it is preferable to prepare correction data for given surrounding environment, e.g., temperature, humidity, etc. Based on such reference data and correction data, the amount of perspiration according to a change in brightness can be immediately measured and calculated.

The conventional art merely determines whether perspiration occurs or not (presence or non-presence of perspiration). In contrast, the present invention can determine not only whether perspiration occurs, but also determine the amount of perspiration. This is because the device and the method according to the present invention measure an amount of perspiration from a change in brightness. Thus, the present invention is advantageous over the conventional art in that the present invention can make a quantitative examination applicable.

In other words, the scope of application of the conventional technology is limited since it merely determines whether perspiration occurs or not. In contrast, the present invention can measure quantitative amount of perspiration. So, it is possible not only to diagnose an abnormal body pant but also to predict a body part where an abnormality might occur in the future. According to the present invention, diagnosis or prediction of imbalance in a human body is capable.

Figure 3:
FIGS. 3A and 3B are diagrams showing the difference in color depending on the amount of perspiration secreted from respective body parts of a person. The difference in color is measured using a device and a method according to the present invention, which measures the amount of perspiration of respective body parts of a person using a change in brightness.
Figure 3A:
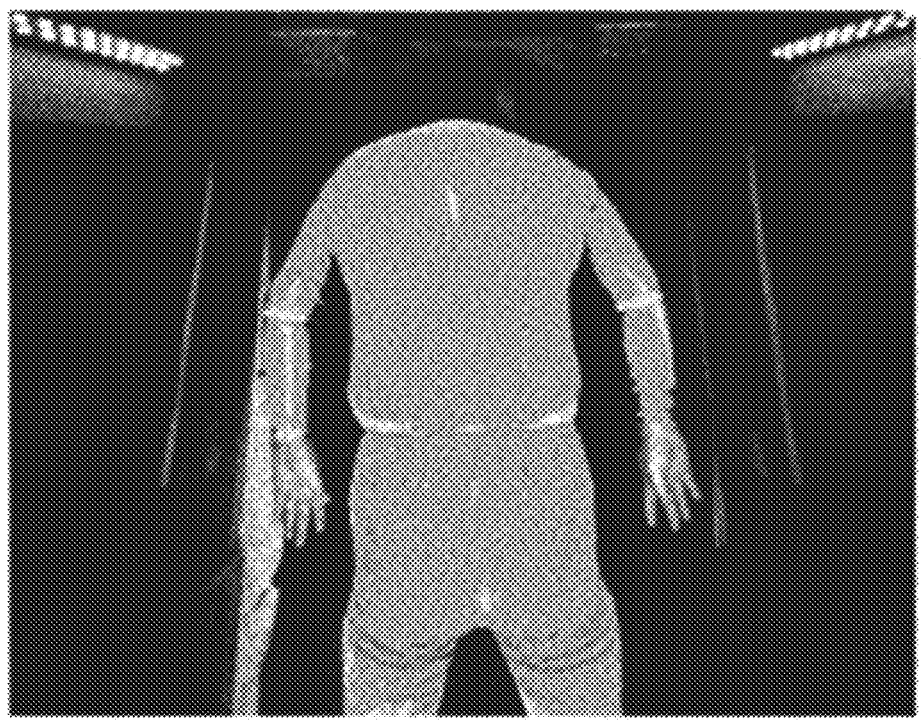
Figure 3B:
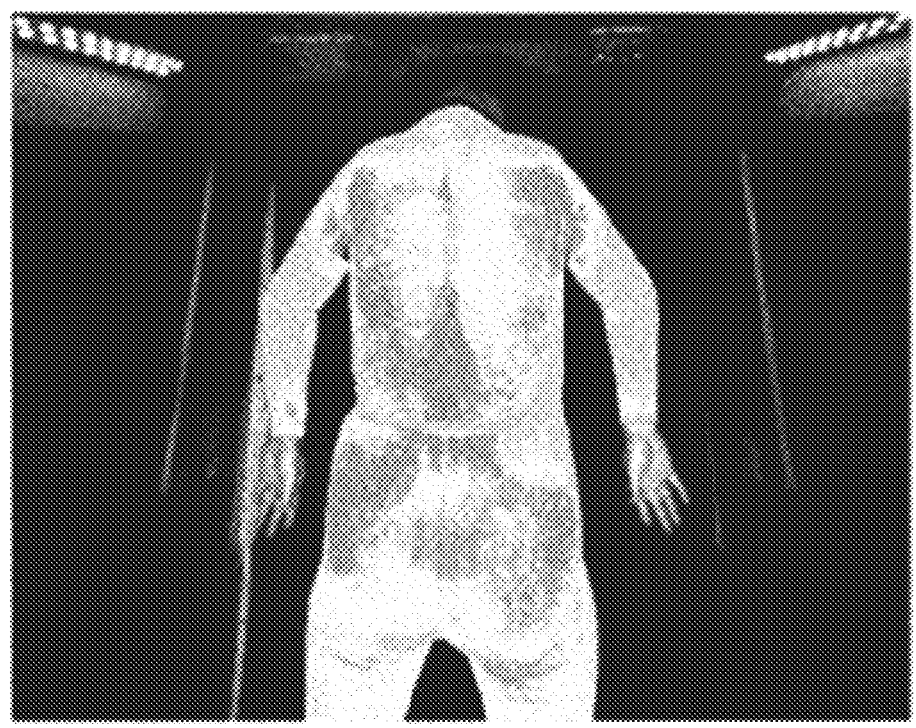

FIGS. 3A and 3B are diagrams showing the difference in color depending on the amount of perspiration secreted from respective body parts of a person.

The difference in color is measured using a device and a method according to the present invention, which measures the amount of perspiration of respective body pans of a person using a change in brightness. Referring to FIG. 3, the brightness change measurer (50) measures the first brightness of the first reflected light of the covering (20) worn by the subject (100) before sweating and the second brightness of the second reflected light of the covering (20) worn by the subject (100) after sweating. Then, the brightness change measurer (50) determines the difference in brightness. The perspiration amount converter (60) automatically converts the difference in brightness into an amount of perspiration.

When the amount of perspiration of a given body part is less than the first perspiration reference point, i.e., 1.95 $\mu l/cm^2$, the given body part is expressed in light blue and light green. When the amount of perspiration of the given body part is between the first perspiration reference point, i.e., 1.95 $\mu l/cm^2$ (inclusive) and the second perspiration reference point, i.e., 2.45 $\mu l/cm^2$ (exclusive), the given body part is expressed in yellow. When the amount of perspiration of the given body part is between the second perspiration reference point, i.e., 2.45 $\mu l/cm^2$ (inclusive) and the third perspiration reference point, i.e., 3.00 $\mu l/cm^2$ (exclusive), the given body part is expressed in orange. When the amount of perspiration of the given body part is the third perspiration reference point, i.e., 3.00 $\mu l/cm^2$ or more, the given body part is expressed in red.

Referring to FIG. 3A, the subject (100) is colored generally in orange. This indicates the amount of perspiration is greater than or equal to the secondary perspiration reference point, 2.45 $\mu l/cm^2$ and is less than the third perspiration reference point, 3.00 $\mu l/cm^2$, presenting that the subject is in a good health condition.

However, the middle part of the back and the elbow part are in light green or yellow. This indicates that the amount of perspiration is (i) less than the first perspiration reference point 1.95 $\mu l/cm^2$ or (ii) between the first perspiration reference point 1.95 $\mu l/cm^2$ (inclusive) and the second perspiration reference point 2.45 $\mu l/cm^2$ (exclusive). This may be interpreted that the body parts are currently in an abnormal state or abnormality is highly likely to occur in the future in those body parts. Thus, the middle part of the back and the elbow need special care.

In addition, according to FIG. 3B, the subject (100) is colored generally in light green or yellow. This indicates that the amount of perspiration is (I) less than the first perspiration reference point 1.95 $\mu l/cm^2$ or (ii) between the first perspiration reference point 1.95 $\mu l/cm^2$ (inclusive) and the second perspiration reference point 2.45 $\mu l/cm^2$ (exclusive).

This may present that that subject is currently in an abnormal state or abnormality is highly likely to occur in the future. Thus, it may be said that the subject is in an abnormal health condition. In particular, the arms and neck are colored in light green. This indicates that the amount of perspiration is less than the first perspiration reference point, 1.95 $\mu l/cm^2$.

This may present that an abnormality or disease has already occurred in those body parts. Thus, the arms and neck need an immediate treatment.

As described above, according to the device and the method of the present invention for measuring the amount of perspiration in respective body parts of a subject using a change in brightness, it is possible to immediately and quantitatively predict (i) whether or not a subject (100) is in an abnormal health condition, (ii) the chance the subject (100) suffers an abnormal health condition in the future, and (iii) whether or not the subject suffers an imbalanced body issues. Therefore, the device and the method of the present invention for measuring the amount of perspiration in respective body parts of a subject using a change in brightness is advantageous in that (i) it can quantitatively detect the amount of perspiration and (ii) it can quantitatively determine dysfunction of autonomic nervous system.

EXPLANATION OF REFERENCE NUMERALS

10: temperature controller
20: Covering
21: perspiration reagent coating layer
22: fabric layer
30: light irradiator
40: reflected light collector
50: brightness change measurer
60: perspiration amount converter
100: subject The above-mentioned embodiments are presented with reference to the drawings. It should be understood that the above-mentioned embodiments are merely examples and various modifications and equivalent are possible by a person having an ordinary skill in the art. Therefore, the scope of the present invention should be determined by the claims in reference to the description presented above.

What is claimed is:

1. A device for measuring an amount of perspiration of respective body parts of a person using a change in brightness, comprising:
    a temperature controller which raises temperature of a subject and induces sweating;
    a covering which is coated with a perspiration reagent and is in contact with a skin of the subject, wherein the perspiration reagent absorbs perspiration and changes its color in response to perspiration;
    a light irradiator which irradiates light to the covering;
    a reflected light collector which collects reflected light reflected from the covering;
    a brightness change measurer which measures a change in brightness of the reflected light collected by the reflected light collector; and
    a perspiration amount converter which converts the change in brightness to an amount of perspiration secreted from respective body parts of the subject,
    wherein the perspiration reagent includes an aqueous ink, wherein the aqueous ink contains acrylic resin,
    wherein the covering includes (i) a fabric layer of 0.20-0.40 mm in thickness and (ii) a perspiration reagent coating layer of 0.03-0.08 mm in thickness,
    wherein the covering coated with the perspiration reagent is in a light blue.

2. The device of claim 1,
    wherein the brightness change measurer measures a brightness index $L^*$ in a color system $L^*a^*b^*$.

3. A device for measuring an amount of perspiration of respective body parts of a person using a change in brightness, comprising:
    a temperature controller which raises temperature of a subject and induces sweating;
    a covering which is coated with a perspiration reagent and is in contact with a skin of the subject, wherein the perspiration reagent absorbs perspiration and changes its color in response to perspiration;
    a light irradiator which irradiates light to the covering;
    a reflected light collector which collects reflected light reflected from the covering;
    a brightness change measurer which measures a change in brightness of the reflected light collected by the reflected light collector; and
    a perspiration amount converter which converts the change in brightness to an amount of perspiration secreted from respective body parts of the subject,
    wherein the brightness change measurer measures a brightness index $L^*$ in a color system $L^*a^*b^*$,
    wherein the brightness change measurer measures a change in brightness at a given body part of the subject using (i) a first sweating reference point, (ii) a second sweating reference point, and (iii) a third sweating reference point,
    wherein, at the first sweating reference point, the brightness index measured by the brightness change measurer drops from 92 to 76, and the amount of perspiration of the given body part is 1.95 $\mu l/cm^2$,
    wherein, at the second sweating reference point, the brightness index measured by the brightness change measurer drops from 76 to 61, and the amount of perspiration of the given body part is 2.45 $\mu l/cm^2$,
    wherein, at the third sweating reference point, the brightness index measured by the brightness change measurer drops from 61 to 44, and the amount of perspiration of the given body part is 3.00 $\mu l/cm^2$.

4. A method for measuring an amount of perspiration of respective body parts of a subject using a change in brightness, comprising:
    a step of placing a covering on a subject to be in contact with each other, wherein the covering is coated with a perspiration reagent, wherein the perspiration reagent absorbs perspiration and changes its color in response to perspiration;
    a step of irradiating light to the covering before sweating;
    a step of collecting a first reflected light, wherein the first reflected light is reflected from the covering before sweating;
    a step of measuring a first brightness of the first reflected light;
    a step of raising body temperature of the subject and induces sweating;
    a step of irradiating light to the covering after sweating, wherein the covering is subject to change its color upon absorption of perspiration;
    a step of collecting a second reflected light which is reflected from the covering after sweating;
    a step of measuring a second brightness of the second reflected light; and
    a step of detecting a change between the first brightness and the second brightness, and converting the change in brightness to an amount of perspiration secreted from respective body parts of the subject,
    wherein the perspiration reagent includes an aqueous ink, wherein the aqueous ink contains acrylic resin, wherein the coating includes (i) a fabric layer of 0.20-0.40 mm in thickness and (ii) a perspiration reagent coating layer of 0.03-0.08 mm in thickness,
wherein the covering coated with the perspiration reagent is colored in a light blue.

5. The method of claim 4,
wherein, in the step of measuring the first brightness of the first reflected light, a brightness index L* is measured in a L*a*b* colorimetric system,
wherein, in the step of measuring the second brightness of the first reflected light, a brightness index L* is measured in a L*a*b* colorimetric system.

6. The method of claim 5,
wherein, each of the first brightness and the second brightness is measured using (i) a first sweating reference point, (ii) a second sweating reference point, and (iii) a third sweating reference point,
wherein the brightness change measurer measures the change in brightness at a given body part using (i) a first sweating reference point, (ii) a second sweating reference point, and (iii) a third sweating reference point
wherein, at the first sweating reference point, the brightness index measured by the brightness change measurer drops from 92 to 76, and the amount of perspiration of the given body part is 1.95 μl/cm$^2$,
wherein, at the second sweating reference point, the brightness index measured by the brightness change measurer drops from 76 to 61, and the amount of perspiration of the given body part is 2.45 μl/cm$^2$,
wherein, at the third sweating reference point, the brightness index measured by the brightness change measurer drops from 61 to 44, and the amount of perspiration of the given body part is 3.00 μl/cm$^2$.

* * * * *